United States Patent [19]

Alex et al.

[11] 4,064,438

[45] Dec. 20, 1977

[54] NONDESTRUCTIVE DETECTION AND MEASUREMENT OF HYDROGEN EMBRITTLEMENT

[75] Inventors: Franklin Alex, Layton; Joseph Gerald Byrne, Salt Lake City, both of Utah

[73] Assignee: The University of Utah, Salt Lake City, Utah

[21] Appl. No.: 653,335

[22] Filed: Jan. 29, 1976

[51] Int. Cl.$^2$ ............................................. G01N 23/00
[52] U.S. Cl. .................................. 250/308; 250/358 R
[58] Field of Search ............................. 250/358 R, 308

[56] References Cited

U.S. PATENT DOCUMENTS

| | | | |
|---|---|---|---|
| 3,593,025 | 7/1971 | Grosskreutz | 250/358 R |
| 3,970,855 | 7/1976 | Holt et al. | 250/358 R |

*Primary Examiner*—Davis L. Willis

[57] ABSTRACT

A nondestructive system and method for the determination of the presence and extent of hydrogen embrittlement in metals, alloys, and other crystalline structures subject thereto. Positron annihilation characteristics of the positron-electron annihilation within the tested material provide unique energy distribution curves for each type of material tested at each respective stage of hydrogen embrittlement. Gamma radiation resulting from such annihilation events is detected and statistically summarized by appropriate instrumentation to reveal the variations of electron activity within the tested material caused by hydrogen embrittlement therein. Such data from controlled tests provides a direct indication of the relative stages of hydrogen embrittlement in the form of unique energy distribution curves which may be utilized as calibration curves for future comparison with field tests to give on-site indication of progressive stages of hydrogen embrittlement.

12 Claims, 1 Drawing Figure

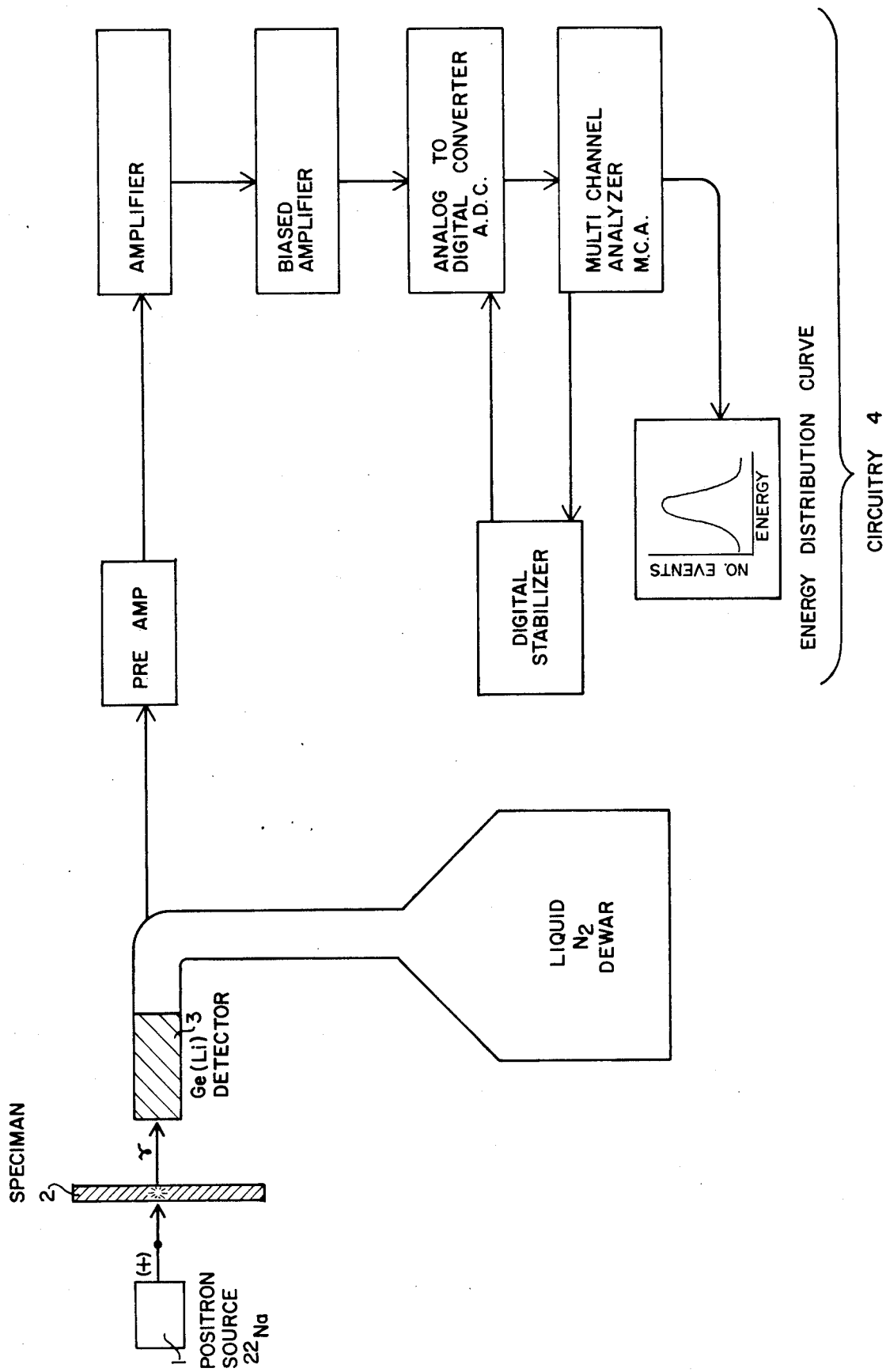

NONDESTRUCTIVE DETECTION AND MEASUREMENT OF HYDROGEN EMBRITTLEMENT

This invention was developed pursuant to Contract No. E(11-1)-2128 with the Energy Research and Development Administration.

BACKGROUND

Although the phenomenon of hydrogen embrittlement has been observed and studied for more than a century, the mechanism which causes the embrittled condition is not yet understood. Hydrogen embrittlement develops in both ferrous and non-ferrous metals and alloys where such materials come in contact with a suitable hydrogen environment. By some unascertained means, the hydrogen atoms or ion invades the crystalline structure of the metal or alloy and disrupt the lattice such that the toughness of the metal or alloy is substantially reduced. Strength reduction can be so severe that the embrittled metal may be advanced to the point of fracturing without any attendant applied stress. Experimentation has demonstrated that high quality steel placed in an acid or electrolysis bath and charged for a period of time to extreme stages of hydrogen embrittlement can be manually crumbled as a result of the hydrogen embrittlement alone. The origin of the hydrogen may be acid solution, electrolysis processes, $H_2$ environment or virtually any material which develops free hydrogen or hydrogen ion. Thus, once the hydrogen has been absorbed into the crystalline structure, knowing its origin is of little importance in predicting the effects of embrittlement.

The severity of these effects will vary with the attendant conditions. Obviously, the longer the duration of exposure of the metal to the hydrogen environment and the greater the surface area of exposed metal, the greater will be the extent of hydrogen absorption. It has also been demonstrated that harder metals tend to be more susceptible to the destrcutive effects of hydrogen embrittlement than metals of a more flexible nature. Furthermore, the process of embrittlement is enhanced by intermediate temperatures and low strain. The occurrence of these favorite conditions can increase the rate of hydrogen absorption into metals by a factor of as much as $10^5$ times that of normal hydrogen solubility.

Hydrogen embrittlement is to be distinguished from "hydrogen attack." The latter occurs at elevated temperatures and pressures, causing decarburization in steels. This results in the formation on intergranular fissures, blistering and other structural damage. Hydrogen embrittlement, on the other hand, does not necessarily involve such severe disruption of the crystalline structure, although some interstitial displacement by the hydrogen may occur. If an alloy is subjected to hydrogen attack, however it appears to be more susceptible to hydrogen embrittlement at lower temperatures—a problem well recognized by refineries, power plants and paper mills.

Practically speaking, hydrogen embrittlement is of great concern in many phases of industry and commercial life. It arises during the fabrication and processing of metals where hydrogen is present in meaningful concentrations in the surrounding environment. It occurs in electroplating and electrolysis processes. Welding is another source of hydrogen embrittlement due to the high temperature/low stress in proximity to the liquid metal in the fusion zone.

The primary public concern regarding hydrogen embrittlement is the fact that there is little warning as to pending catastrophic failure where the embrittlement is not accompanied by severe structural deformation such as that normally associated with fatigue dislocations and voids. The consequence is a delayed occurrence of failure in the metal which heretofore was unpredictable. Whereas current techniques enable the estimation of useful-life of metal being regularly subjected to known stress and fatigue, the only processes previously understood as useful to make such predictions concerning the extent hydrogen embrittlement have essentially required the destructive analysis of the subject metal. Such procedures defeat the purpose of prediction since the metal must be replaced in part to make the analysis.

The lack of a nondestructive method which reveals the embrittled condition caused by hydrogen absorption has precluded the development of a technique which enables the monitoring of progressive states of hydrogen embrittlement as the metal approaches the point of failure. Furthermore, the development of such a technique would permit the prediction of expected failures, enabling replacement within known safety limits and at lower cost due to the resultant controlled replacement.

The positron annihilation technique for analyzing crystalline structure and lattice defects has been understood since 1950; however, it has never been applied to hydrogen embrittlement. Research by Joseph C. Grosskreutz, as disclosed in U.S. Pat. No. 3,593,025 entitled "Detecting Defects by Distribution of Positron Lifetimes in Crystalline Materials," discusses the application of this technique to analysis of fatigue and stress damage in metals, but fails to suggest potential use of positron annihilation in non-stress related problems such as hydrogen embrittlement.

The reason for such application to the area of stress and fatigue damage in metals was based on the theory that the resulting voids, cracks, and dislocations within the crystalline lattice caused extension of positron lifetime within the metal "due to trapping of the positrons within the voids caused by such crystal defects." The absence of electron density within these voids decreases the frequency of annihilation between such electrons and the invading positrons, thereby extending positron lifetime. The essence, therefore, of the positron annihilation techiques used by Grosskreutz and others in this field of metal analysis relies on the presence of voids within the metal. Indeed, their studies in this field have been directed to materials subjected to stress and fatigue because these conditions are known to cause such defects.

The referred patent, however, does not deal with the nonstress related condition known as hydrogen embrittlement. The two catagories of defects addressed in the specification are fatigue defects and microporosity. Quoting from column one of the patent, "Micropores are accumulation of vacancies (vacancy clusters) in the crystal . . ." The disclosure refers to such defects as arising from fabrication, molding and machining—all stress related processes. It should be noted, therefore, that 35 USC 112 limits the application of this patent to art dealing with detection of voids, dislocations, vacancies and similar defects resulting from fatigue and stress. This is not the unique analysis required for detection of non-stress condition of hydrogen embrittlement.

Therefore, the application of positron annihilation techniques to the detection of hydrogen embrittlement in metals and similar crystalline structures has not heretofore been conceptualized. Since hydrogen embrittlement apparently occurs where hydrogen ions are dispersed through the lattice prior to any formation of voids and other fatigue related defects, the theoretical basis disclosed in the above reference material does not suggest that positron annihilation is a useful technique for hydrogen embrittlement analysis. In fact, the only prior methods conceivably useful for detection of hydrogen embrittlement have involved quantitative detection of hydrogen by either nondestructively extracting the hydrogen by subjection of the material to high heat or destructively extracting the hydrogen from a sample of the subject metal by fusion techniques. The very fact that these quantitative processes have been the sole method for detection of hydrogen embrittlement strongly suggests that the research of Grosskreutz, when viewed in connection with the state of the art, did not teach or even suggest the potential application of positron annihilation as a non-destructive method for detecting the presence of hydrogen embrittlement.

Technically, the occurrence of hydrogen embrittlement is uniquely distinct from the characteristics and consequences of the application of fatigue and stress to crystalline structure. Where fatigue defects are best developed at high strain rates and low temperatures, hydrogen embrittlement prefers low strain and higher temperatures. It will be further noted that the application of the positron annihilation technique in hydrogen embrittlement detection involves a more complicated positron lifetime response which appears to be inconsistent with the predictions of the Grosskreutz patent.

Instead of a simple increase in positron lifetime with increased defects as indicated by Grosskreutz, the progressive stages of hydrogen embrittlement are accompanied by an initial increase followed by a subsequent decrease lifetime duration. Such a response is incompatible with the Grosskreutz disclosure. This distinction is discussed in greater detail in the detailed description.

BRIEF SUMMARY AND OBJECTS OF THE INVENTION

The present invention relates to a nondestrucive method for the detection and measurement of hydrogen embrittlement in metals, alloys and other crystalline structures subject thereto. The material to be tested is exposed to positrons which enter the crystalline lattice of the material and annihilate with electrons therein. The annihilation process yields gamma radiation whose energy levels define the relative variations of electron activity which indicates the extent of hydrogen embrittlement within the material. This resultant gamma radiation can be detected by instrumentation designed to measure and record the data relating to each detected annihilation, thereby creating a statistical summary of the annihilation characteristics in the form of energy distribution curves. Such curves can be developed for various classes of metals of known levels of hydrogen embrittlement, to be utilized as reference standards to indicate the stage of unknown embrittlement within a given metal.

The primary annihilation characteristic comprehended by the present invention is the Doppler shift of the gamma radiation due to annihilation with electrons of various velocities. By utilizing a standard Ge (Li) Detector and associated circuitry, the resulting energy curve can be promptly displayed for making an on-site analysis with the reference standards. The resulting combination is a portable testing unit capable of field evaluations, which has heretofore been impossible.

It is therefore an object of the present invention to provide a method for the nondestructive determination of hydrogen embrittlement in metals, alloys and crystalline materials subject thereto.

It is a further object of the present invention to provide a method for nondestructively measuring the extent of such embrittlement and of projecting the remaining life of the tested material.

It is another object of this invention to provide the additional benefit of a portable field-use capability to the previously indicated objectives.

These and other objects and features of the present invention will become more fully apparent from the following description and appended claims taken in conjunction with the accompanying drawing.

DESCRIPTION OF THE DRAWING

The FIGURE included herewith represents one of the methods of hydrogen embrittlement detection which measures the Doppler Shift variations of the emitted gamma ray.

DETAILED DESCRIPTION OF THE PREFERRED EMBODIMENTS:

Although there is no unifying theory as to exactly how hydrogen produces the embrittled condition within the crystalline structure, the utility of positron annihilation as a method for determining the presence of the condition has been experimentally verified. The effectiveness of positron analysis is undoubtedly due in part to the sensitivity of the positron particle to the effective electrical charges within the material examined. In non-embrittled crystalline materials, the lattice structure is essentially uniform and therefore the average effects remain characteristically the same.

The infusion of hydrogen into the lattice structure, however, apparently has sufficient effects upon the electrons and invading positrons to register a variance from the normal annihilation characteristics of positrons in a hydrogen-free lattice structure. These variations have been studied and demonstrated to follow specific patterns of response, depending upon the extent of hydrogen embrittlement. Specifically the condition of hydrogen embrittlement is signaled by apparent decrease in electron velocity in softer or annealed metals and an apparent increase in harder metals. Where the metal is of intermediate hardness, an initial increase in electron velocity is followed by a similar decrease upon increased hydrogen embrittlement.

There are at least three characteristics of the positron-electron annihilation which may be utilized to study the extent of hydrogen embrittlement: (1) the measurement of the Doppler energy broadening of gamma rays which accompany the annihilation event, (2) the determination of the corresponding angular correlation of the two emerging gamma rays, and (3) the measurement of positron lifetime. The preferred technique for the present invention involves measurement of changes in the kinetic energy of the electrons within the material, utilizing the Doppler broadening characteristic experienced by emitted gamma rays from the positron-electron annihilation.

Positrons are directed from a suitable source 1, in this case $^{22}Na$, toward the specimen material to be analyzed 2. Annihilation occurs within the material upon collision of the positron with an electron. The resulting conversion of matter to energy yields two diametrically opposed 0.511 Mev gamma rays. Where the center of mass of the annihilating positron-electron pair is in motion, the kinetic energy is conserved through the annihilation process and results in a slight variation of the energy of the 0.511 Mev gamma ray corresponding to such relative motion. These energy variations which appear as a Doppler shift from the exact 0.511 Mev energy, can be detected by any suitably responsive device 3. In the present invention a Ge (Li) Detector is utilized because of its high sensitivity to slight variations of this type.

This apparatus is more fully described in West, R. N., "Positron Studies of Condensed Matter " Monographs on Physics, 1974, Barnes and Noble, p. 12. When a statistical distribution of these gamma rays is recorded, a graphic curve may be produced representing the number of annihilations versus the respective radiation energies. These curves are unique for each stage of hydrogen embrittlement and for each crystalline material tested. Utilizing the circuitry 4 suggested in the figure, an immediate read-out of such distribution curves can be accomplished with a multi channel analyzer 5. Such circuitry is commonly utilized with the Ge (Li) Detector and is available in the commercial market.

Since each crystalline material is unique in response to positron annihilation techniques, a standard set of calibration curves must be developed in order to enable nondestructive analysis. Ideally, a specimen can be separated from the production run in a manufacturing process and analyzed, with suitable graph-records made. The material is then subjected to the prospective hydrogen environment and periodic energy distribution curves are made until the material is embrittled to a predetermined stage. As the degree of hydrogen embrittlement is increased, these curves initially become more sharply peaked and then broaden with continued embrittlement. This series of distribution curves serve as the graphic history of embrittlement against which future tests can be matched and classified.

More specifically, a graphic record is quickly and inexpensively developed for a specimen of alloy by subjecting such a specimen to an electrolytic charging bath which induces hydrogen into the alloy structure. Distribution curves are then recorded at intervals over the period of charging until the metal spontaneously fractures. Utilyzing these calibration graphs as a reference, the actual alloy product (be it pipeline, wire, etc.) can be later scanned with the Ge (Li) Detector and an estimation made as to the progress of hydrogen embrittlement.

By way of illustration such a record might include a set of ten curves taken at five minute intervals, each successive graph having a bell-shaped curve with a somewhat sharper or broader peak than the previous graph. Subsequently, when a future on-site test reveals a distribution curve comparible to calibration specimen "five" of the 10 graph series, a conclusion that the material was half way to spontaneous no-stress failure would be warranted.

It should be apparent that numerous calibration techniques may be developed to provide the graphic standards for future comparison. Often, the method for calibration of specimens will depend upon the type of material and projected use. Where the metal or alloy to be monitored is subject to concurrent stress and fatigue, proper calibration should attempt to simulate such an environment.

Furthermore, the desired degree of accuracy is a factor in determining when a new calibration specimen is required. A single set of predetermined specimen curves may suffice for general analysis of any specific alloy (i.e. 4340 steel) regardless of manufacturing source, provided extreme accuracy is not important. Where such accuracy is critical to the monitoring of hydrogen embrittlement, however, the preferred method of calibration would require the development of a special set of specimen curves taken from the very metal to be monitored.

Conventional hydrogen embrittlement tests can be coordinated with the positron annihilation method to confirm that the hydrogen absorption is accompanied by the embrittling condition. Mere extraction of hydrogen from the material being charged therewith does not by itself confirm this condition because hydrogen concentration is not directly indicative of the extent of embrittlement. Consequently, heating or fusing the sample would not ensure a true measure of the degree of hydrogen embrittlement. A concurrent stress analysis such as subjecting notched, cylindrical bar samples of the material to known stress loads at each stage of positron analysis provides a coordinated confirmation of the embrittled condition being demonstrated by the various energy distribution curves. The relevant experimental data for each stage of embrittlement is indicated in a data summary on the respective specimen curves.

As indicated previously, a primary benefit of the use of Doppler shift positron analysis is the mobility of the test equipment. A field testing system as illustrated in the figure is transported by truck or other means to various locations for on-site analysis. Once the standard specimen curves are compiled, the system provides momentary readout and allows instantaneous evaluation as to the embrittlement stage by matching the on-site curve with the similar specimen calibration curve. The degree of hydrogen embrittlement and projected remaining useful-life is read directly from the accompanying data summary.

Although the other methods of positron analysis (angular correlation and lifetime measurement) are less easily adapted for field use, they are equally effective in demonstrating the condition of hydrogen embrittlement. The angular correlation technique measures the angular separation of the two 0.511 Mev gamma rays emitted upon annihilation of the positron with an electron. Where the center of mass of the annihilating pair is at rest, the gamma rays emerge at 180° divergence. If the center of mass is in motion, however, the momentum is conserved by a slight deviation from this 180° angle. The equipment for detecting this deviation is common to the art and is suitably disclosed in West, R. N. "Positron Studies of Condensed Matter," Monographs on Physics, 1974, Barnes and Noble p. 10. Since the relative electron velocities here are likewise the subject of measurement, distribution curves similar to those developed from the Doppler shift may be utilized for analysis of the stage of embrittlement.

The detection of hydrogen embrittlement by positron lifetime measurements is essentially accomplished in the same system as outlined by R. E. Bell, Jr. of Nuclear Instrumentation Methods, Vol. 55, p. 1. This system is a more contemporary form for the same procedures outlined by Grosskreutz as disclosed by that patent referenced herein. Such systems utilize the isotope $^{22}$Na which emits a 1.28 Mev Gamma ray concurrently with the birth of the positron. The time interval between this event and the subsequent detection of the 0.511 Mev annihilation gamma ray reveals the lifetime of the positron. As with the energy distribution curves of the previous methods, the positron lifetime observations illustrate similar patterns when the condition of hydrogen embrittlement is present.

Such observations fall into three general catagories, depending upon the physical characteristics of the material tested. Where the metal is quite soft or annealed, an increase of hydrogen embrittlement results in a corresponding increase in the measured lifetime of the positron. If, however, the metal is initially at its maximum hardness level, the absorption of hydrogen within the metal structure results in a decrease in the positron lifetime. Those metals having an intermediate hardness, first experience an initial increase in positron lifetime and then a subsequent decrease during the progressive hydrogen embrittlement stages. Here again, standard calibration readings would be necessary for each type of metal to be examined, with future positron lifetime measurements being evaluated against the appropriate standards.

It is understood that the aforementioned methods of positron analysis for hydrogen embrittlement are merely illustrative of numerous potential techniques utilizing positron annihilation. It is intended that all improvements or changes which come within the meaning and range of equivalency of the following claims are to be embraced within their scope.

What is claimed and desired to be secured by the United States Letters Patent is:

1. A method for the nondestructive determination of hydrogen embrittlement in metals, alloys, and other crystalline materials subject thereto, comprising the steps of:
   a. exposing the subject material to positron radiation,
   b. detecting the resultant positron-electron annihilation characteristics, and
   c. recording the resultant data from numerous annihilation events in statistical format appropriate for evaluation of the electron activity within the subject material.

2. A method as defined in claim 1, wherein the variation of annihilation characteristics within the tested material are indicated by detecting the Doppler shift variations of a 0.511 Mev gamma ray.

3. A method as defined in claim 1, wherein the annihilation characteristics of the tested material are detected by the analysis of angular correlation between two concurrently emitted 0.511 Mev gamma rays.

4. A method as defined in claim 1, wherein the variations in annihilation characteristics within the tested material are detected by positron lifetime measurements.

5. A method as defined in claim 1, wherein the statistical format comprises an energy distribution curve representing a specific material at a specific stage of hydrogen embrittlement.

6. A method as defined in claim 5, wherein is provided the additional step of compiling multiple energy distribution curves at various stages of embrittlement of specific metals for use as calibrated standards for future test comparisons.

7. A system for the nondestructive determination of hydrogen embrittlement in metals, alloys and other crystalline materials subject thereto, comprising:
   a. a source of positron radiation,
   b. means for exposing the specified material to be tested to said positron radiation, and
   c. means for detecting the resultant positron-electron annihilation characteristics of the specified material.

8. A system as defined by claim 7, wherein the detecting means is an instrument capable of distinguishing the variations of the Doppler shift of the emitted 0.511 annihilation gamma rays.

9. A system as defined by claim 8, wherein the detecting means is a Ge (Li) Detector.

10. A system as defined by claim 7, wherein the detecting means is an instrument capable of measuring the angular correlation between the emerging 0.511 Mev gamma rays emitted upon positron-electron annihilation.

11. A system as defined by claim 7, wherein the detecting means is an instrument capable of measuring the relative lifetimes of the radiated positrons.

12. A system as defined in claim 7, further comprising a means for recording the annihilation characteristics in statistical format appropriate for evaluation of electron activity within the subject material.

* * * * *